United States Patent

White et al.

[11] Patent Number: 5,905,570
[45] Date of Patent: May 18, 1999

[54] REMOTE ELECTRO-OPTICAL SENSOR SYSTEM FOR WATER QUALITY MONITORING

[75] Inventors: Brian N. White, Los Alamitos; John H. Morrow, La Jolla, both of Calif.

[73] Assignee: Department of Water and Power City of Los Angeles, Los Angeles, Calif.

[21] Appl. No.: 08/933,340

[22] Filed: Sep. 18, 1997

[51] Int. Cl.[6] .................................................. G01N 21/62
[52] U.S. Cl. .......................... 356/317; 356/318; 356/417; 250/458.1; 250/459.1; 250/461.1
[58] Field of Search .................................... 356/317, 318, 356/417; 250/458.1, 459.1, 461.1

[56] References Cited

U.S. PATENT DOCUMENTS 4,804,849  2/1989  Booth et al. ............................ 356/417
4,963,024  10/1990  Ulich ........................................ 356/342

OTHER PUBLICATIONS

Brian N. White, *Remote Biological Monitoring in an Open Finished–Water Reservoir*, Sep. 1991, American Water Works Association Journal, 83:107–111.

*Primary Examiner*—Robert H. Kim
*Assistant Examiner*—Zandra V. Smith
*Attorney, Agent, or Firm*—Thomas I. Rozsa; Tony D. Chen; Jerry Fong

[57] ABSTRACT

An improved water quality monitoring system and method. The system utilizes reflectance radiometers to provide multiple wavelength measurement of downwelling irradiance and/or upwelling radiance. The method calculates attenuation coefficients from the downwelling irradiance or upwelling radiance to derive chlorophyll concentration in the water.

21 Claims, 14 Drawing Sheets

REOS-3 DAILY OPERATIONS REPORT
HOLLYWOOD RESERVOIR
07-MAY-97

PRINTED 5/8/97
JULIAN DATE: 127
REOSnt REPORT 3.4

|  | PRR-2M | PRR-8M | YSI-10M | UNITS |
|---|---|---|---|---|
| ACTUAL DEPTH | 2.1 | 7.7 | 10.3 | METERS |
| TEMPERATURE | 19.8 | 19.1 | 19.2 | DEG.CELSIUS |
| CHLOROPHYLL | 0.6 |  |  | MG.M-3 |
| CALCULATED TRANSPARENCY | 6.5 |  |  | METERS |
| APPARENT TURBIDITY | 0.7 |  |  | TE |
| kPAR | 0.2 |  |  | METER-1 |
| U/W PAR | 604.6 | 190.6 |  | uE.m-2.SEC-1 |
| SURFACE PAR | 876.7 |  |  | uE.m-2.SEC-1 |
| ORP |  |  | 499 | mVOLTS |
| SPECIFIC CONDUCTANCE |  |  | 0.4 | mSm.cm-1 |
| CONDUCTIVITY |  |  | 0.3 | mSm.cm-1 |

SOURCE FILE NAME HOL97127_RAW.CSV

THE FOLLOWING PAGES SHOW THE TIME SERIES OF THE VARIOUS PARAMETERS
FOR THE RESERVOIR THE VALUES ABOVE ARE DAILY AVERAGES.
NIGHT VALUES ARE NOT USED IN AVERAGES FOR OPTICAL SENSORS.

TIME COMMENT

5/7/97 12:00:05 AM BEGINNING OF A NEW DAY
5/7/97 12:05:58 AM BEGINNING OF A NEW DAY

FIG.3

REMOTE ELECTRO-OPTICAL SENSOR SYSTEM FOR WATER QUALITY MONITORING

BACKGROUND OF THE INVENTION

1. Field of the Invention

The present invention generally relates to the field of water quality monitoring devices. More particularly, the present invention relates to the field of water quality monitoring devices utilizing the remote electro-optical sensor (REOS) system.

2. Description of the Prior Art

The general acronym REOS (Remote Electro-Optical Sensor) refers to moored in-reservoir water quality monitoring systems. REOS systems provided the first continuous in-reservoir monitoring of nuisance phytoplankton populations in drinking water reservoirs. Prior to the development of REOS technology, laboratory inspection of reservoir water samples was needed to track algal population dynamics.

A prototype system (REOS-1) and a subsequent developmental system (REOS-2) were deployed by the Los Angeles Department of Water and Power (LADWP) in 1989 and 1992, respectively, as described in White, B. N., Kiefer, D. A., Morrow, J. H. and G. F. Stolarik (1991), *Remote Biological Monitoring in an Open Finished-Water Reservoir*, American Water Works Association Journal, 83:107–111.

REOS-1 and REOS-2 systems were designed specifically to monitor nuisance algal populations by making accurate measurements of the red fluoresced light, stimulated by ambient sunlight, which radiates from all eukaryotic (higher plant) phytoplankton during photosynthesis. Research primarily on marine phytoplankton has shown that the fluorescent flux can be related both to chlorophyll concentration and to instantaneous rates of photosynthesis.

The REOS-1 and REOS-2 systems utilized specialized instruments, including profiling natural fluorometers (PNF), to measure both photosynthetically active radiation (PAR) between 400–700 nm as well as the red fluorescence emitted from the phytoplankton crop. The fluorescence signal is measured directly as the upwelling (nadir) radiance over the relatively broad bandwidth of chlorophyll fluorescence. The measurement is different from chlorophyll fluorescence measured using a strobe fluorometer in that the fluorescence signal results from the same source as that driving photosynthesis in situ.

The prototype REOS-1 system used a single PNF to monitor the phytoplankton crop. Since the PNF measures upwelling radiance directly below the sensor and samples a volume approximately 5 meters below the instrument in clear waters, the developmental REOS-2 system incorporated additional PNF's to increase optical coverage of the water column. In addition to the optical measurements, the REOS-2 system measures pH, dissolved oxygen (DO), oxidation/reduction potential (ORP) and conductivity. The REOS-2 system also utilized a dedicated 80486-microprocessor based remote access workstation (RAW) to control the system, acquire the data from each instrument, and perform functions for remote telemetry of the data.

It is desirable to develop a fully automated REOS system utilizing multiple regions of the spectrum which records and reports the status of a wider variety of water quality variables in open drinking water reservoirs, and thereby provides reservoir managers with the means to detect and intercept impending phytoplankton blooms before taste, odor, and appearance problems arise and to optimize the algicidal treatments needed to maintain control of phytoplanktonic growth.

SUMMARY OF THE INVENTION

The present invention is an improved REOS water quality monitoring system. It is developed from the prototype REOS-1 and developmental REOS-2 systems and will be referred to as the REOS-3 system.

REOS-3 system is an improved moored water quality monitoring system that automatically records and reports the status of a wide variety of water quality variables in open drinking water reservoirs. It is designed to continuously monitor nuisance algal populations, thereby providing reservoir managers with the means to detect and intercept impending phytoplankton blooms before taste, odor, and appearance problems arise and to optimize the algicidal treatments needed to maintain control of phytoplanktonic growth. The REOS-3 system is the first moored in-reservoir monitoring system which provides integrated water column values for chlorophyll concentration and turbidity equivalents in addition to spectral light attenuation coefficients and reflectance measurements. It is also the first moored in-reservoir phytoplankton monitoring system which supports fully automated database and report functions.

Described generally, the present invention is an improved water quality monitoring system. The system is comprised of a mooring assembly for suspending an array of electronic measurement instruments or devices underwater. The instruments or devices include at least one reflectance radiometer (RR) which measures multiple wavelengths of upwelling radiance and utilizes a cosine collector to measure multiple wavelengths of downwelling irradiance. These multiple wavelength measurements can be used to calculate chlorophyll concentration in the water. The system also comprises a remote data spooler device for communicating the data measured by the underwater measurement equipment to a remote access workstation, which is used for processing and storing the data.

Described alternatively, the present invention is an improved method of monitoring water quality. The method is comprised of the steps for using a mooring assembly to suspend an array of measurement equipment underwater, and utilizing at least one RR to measure multiple wavelengths of upwelling radiance. The RR also utilizes a cosine collector to measure multiple wavelengths of downwelling irradiance. The method also includes the steps for communicating data measured by the underwater measurement equipment to a remote access workstation for data processing, storage and transmittal, and calculating attenuation coefficients from the downwelling irradiance or upwelling radiance to derive chlorophyll concentration in the water.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 3 is an illustrative sample of the "Daily Operation Report" generated by the present invention REOS-3 system.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
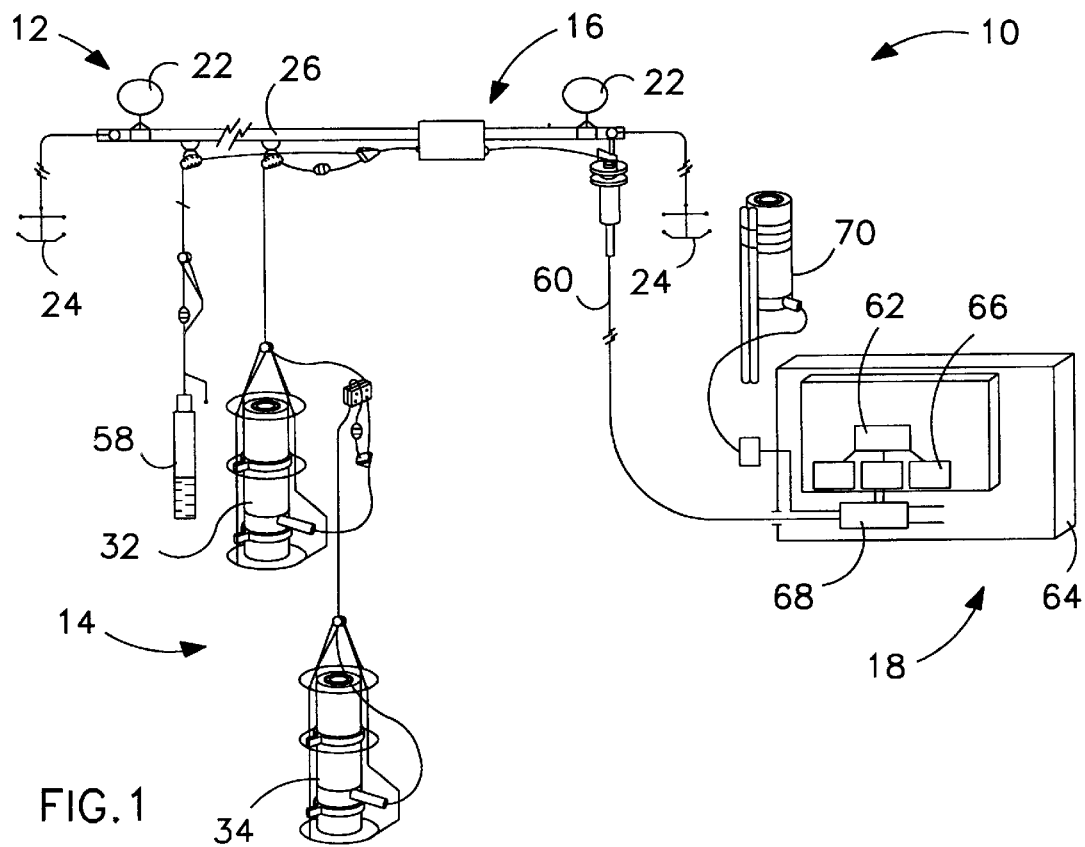
FIG. 1 is an illustrative diagram showing one of the preferred embodiments of the present invention improved REOS system.

Referring to FIG. 1, there is shown the illustration of a REOS-3 system 10 as one of the preferred embodiments of the present invention. The REOS-3 system 10 includes a mooring assembly 12, an array of underwater measurement devices 14, a remote data spooler (RDS) device 16, and a remote access workstation (RAW) 18.

The mooring assembly 12 includes one or more surface floats 22 which may be stabilized by anchors 24. The purpose of the mooring assembly is to moor the array of underwater measurement devices 14 as well as the RDS device 16. The mooring assembly utilizes mooring cables 26 such as 18-10 SO Neoprene coated submersible cables. Stainless steel material is utilized to minimize any shadow by the mooring assembly itself.

The array of measurement devices 14 includes one or more reflectance radiometers (RR). In the preferred embodiment shown in FIG. 1, two (2) RRs 32, 34 are used. The reflectance radiometers measure spectral radiance and irradiance and are designed to monitor chlorophyll fluorescence as well as changes in the reflectance and attenuation coefficients at selected additional regions of the visible and ultraviolet (UV) spectrum, and to provide full coverage of the water column between the instruments. The REOS-3 system utilizes RRs to measure spectral downwelling irradiance (Ed) using a flat collector $2\pi$ steradians solid angle (i.e., a "cosine" collector specifically designed to achieve a response that is proportional to the cosine of the angle of incident light). This is in contrast to the REOS-1 and REOS-2 systems which utilized PNFs to measure scalar irradiance (Eo) over PAR and which used a spherical collector to achieve a constant directional response over nearly $4\pi$ steradians solid angle (i.e., a scalar collector that responds to photons independently of the radiance distribution of the light field).

Figure 2:
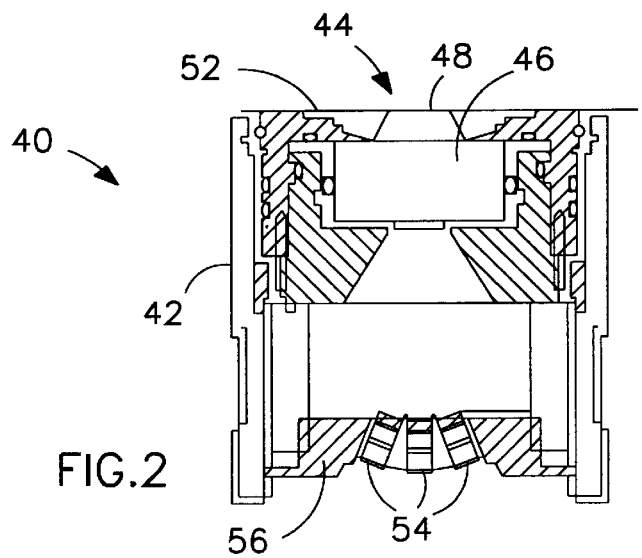
FIG. 2 is an illustrative diagram of a preferred embodiment of the cosine collector utilized in the present invention improved REOS system.

Referring to FIG. 2, there is shown at 40 a preferred embodiment of the cosine collector utilized in the present invention REOS-3 system. The cosine collector 40 for the RRs 32, 34 was designed to meet the specifications of the NASA SeaWiFS Ocean Optics Protocols. It has tubular housing 42. An irradiance diffuser 44 is installed at the top opening of the housing 42. The irradiance diffuser 44 has a raised trapezoidal quartz or acrylic piece 46 covered with a thin sheet of vacuum-formed Teflon® 48 which acts as a diffuser. Since the upper Teflon® surface 48 reflects light at large angles of incidence which results in significant under reporting of the flux, the sides of the trapezoid 46 are raised to provide a surface with a reduced angle of incidence, thereby increasing the response from larger zenith angles. In addition, since a cosine collector should not report light from angles greater than 90 degrees, an outer rim 52 raised to the level of the top of the diffuser 40 is used to act as an occluding ring.

A multiplicity of photodiodes 54 are arranged in an array at the bottom of the diode holder 56, and all view the same area of the bottom of the diffuser 44. This arrangement enables multiple wavelength measurements.

The downwelling irradiance collector 40 utilized on the RRs 32, 34 significantly reduces the overestimates of irradiance at a depth from light reflected from the bottom of shallow reservoirs. As a result, calculations of attenuation coefficient are significantly improved.

The RRs 32, 34 are designed to address the need for a small, modestly-priced, multichannel spectroradiometer to support ocean color research such as the SeaWiFS Program. Each RRs feature a total of 14 optical channels: seven (7) of downwelling irradiance (including UV) viewed through a common cosine collector and seven (7) of upwelling radiance. In addition, the RRs are also able to measure temperature, pressure/depth, etc. RR 32 may be located near the water surface, e.g., at two (2) meter depth, whereas RR 34 may be located at seven (7) meter below the water surface (i.e., about five (5) meters below RR 32).

Referring back to FIG. 1, the array of measurement devices may optionally include additional sensors 58 for measuring pH, DO, ORP, etc.

The function of the RDS device 16 is to transfer the data collected by the array of measurement devices 14 to the RAW 18 through cable or wireless communication. In FIG. 1 a cable connection 60 is shown. Such cable 60 may be a dual conductor, armored steel hydrowire cable.

Data acquisition, system power, and telemetry requirements are performed by the RAW 18. The RAW 18 is designed specifically for the unattended operation of the REOS-3 system in inhospitable environments. It includes a microprocessor-based computer system 62 which is housed in a NEMA Type 4 certified enclosure 64 to protect the control system components from the elements. In addition to system control, the RAW 18 provides isolated power for all REOS-3 components, as well as wired or wireless communication capability, to communicate with the RDS device 16, and to support direct data access to the RAW from a central domain controller (not shown), through its communication interfaces 66 and an intercommunication box 68. In addition, a surface RR 70 may be used to measure downwelling irradiance at the surface. The RDS device 16 (if in wired communication arrangement), and the surface RR 70, are all connected to the computer system interfaces 66 via the intercommunication box 68.

The specially developed RAW data acquisition software retrieves surface and subsurface measurement data through the computer system interfaces 66. The RAW continuously acquires, averages, and stores all sensor data as voltages on a programmed schedule. Two or more separate CSV files are acquired each day: a data file consisting of a time period, i.e. 15 minute, averages for each measured variable and a log file showing the general operation status of the system. An access database containing information on the system configuration resides on the RAW. A central domain controller (not shown) polls each RAW in various locations on a programmed schedule and transfers the daily CSV files using commercially available programs such as Microsoft Windows NT® via wired or wireless communication devices. The voltage data is converted to engineering units in an access database and appended to daily and cumulative tables and reports residing on the central domain controller. The central domain controller automatically prints a daily report for each REOS-3 reservoir each day and exports the reports to selected locations.

FIG. 3 shows a sample of the "Daily Operation Report" generated by the present invention REOS-3 system. It contains the data obtained by the RR 32 at 2 meters, by the RR 34 at 8 meters, and by the sensors 58 at 10 meters. This data includes actual depth, temperature, chlorophyll, calculated transparency, apparent turbidity, kPAR, underwater (U/W) PAR, surface PAR, ORP, specific conductance, conductivity, etc.

Figure 3A:
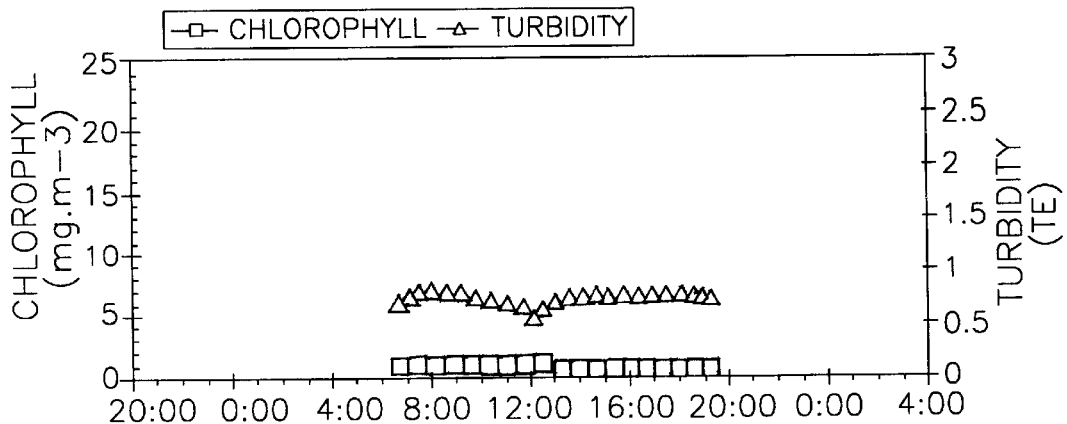
FIG. 3(a) is a plot diagram showing chlorophyll and turbidity curves generated by the present invention REOS-3 system.
Figure 3B:
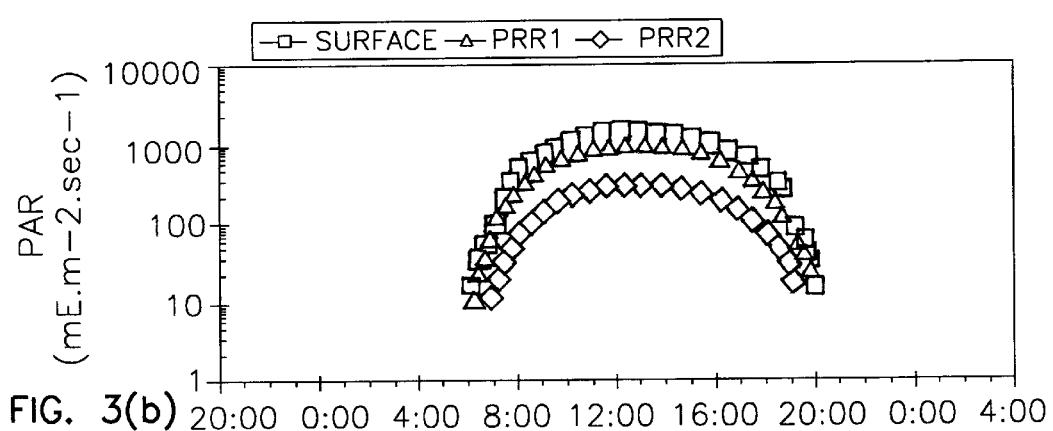
FIG. 3(b) is a plot diagram showing surface and U/W PAR curves generated by the present invention REOS-3 system.
Figure 3C:
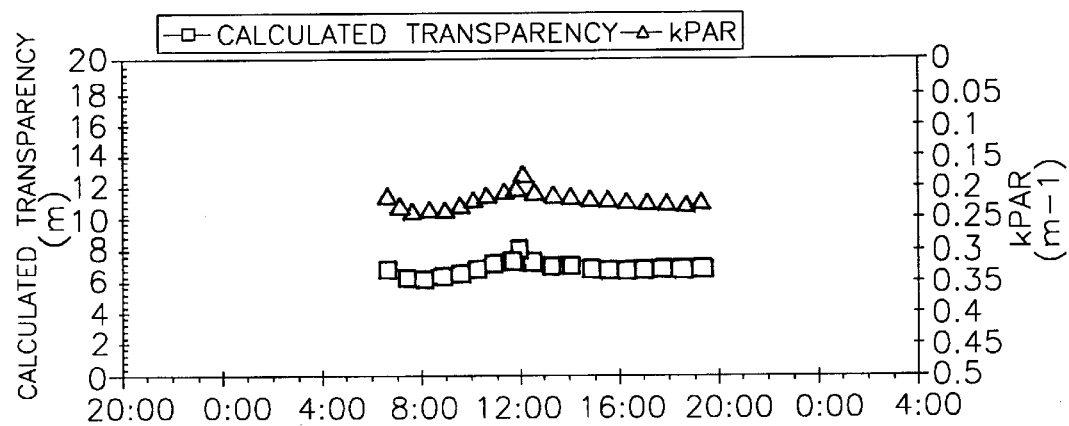
FIG. 3(c) is a plot diagram showing calculated transparency and kPAR curves generated by the present invention REOS-3 system.
Figure 3D:
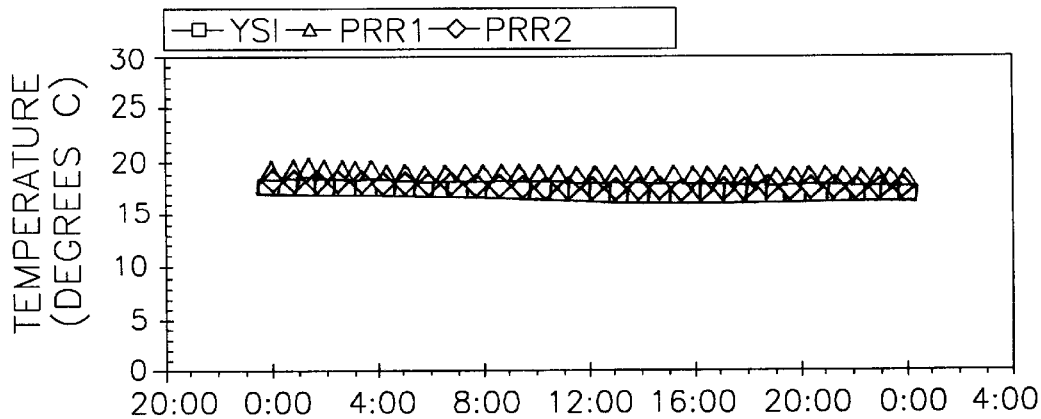
FIG. 3(d) is a plot diagram showing temperature curves generated by the present invention REOS-3 system.
Figure 3E:
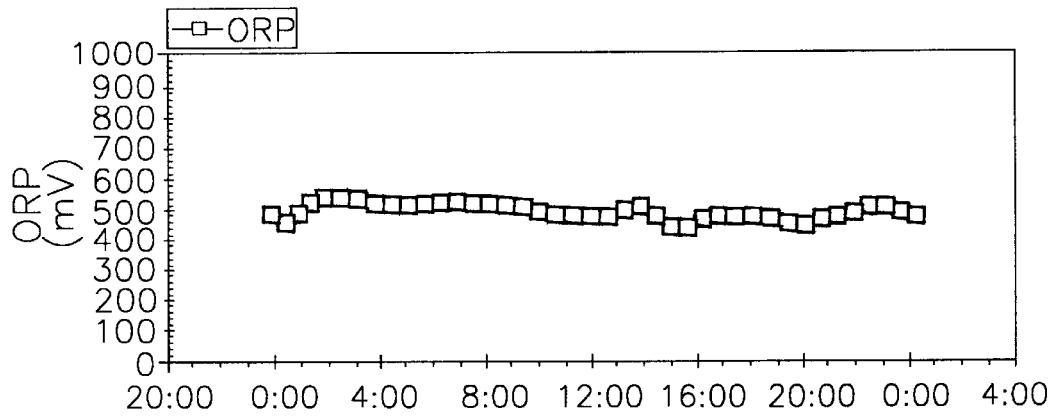
FIG. 3(e) is a plot diagram showing ORP curve generated by the present invention REOS-3 system.
Figure 3F:
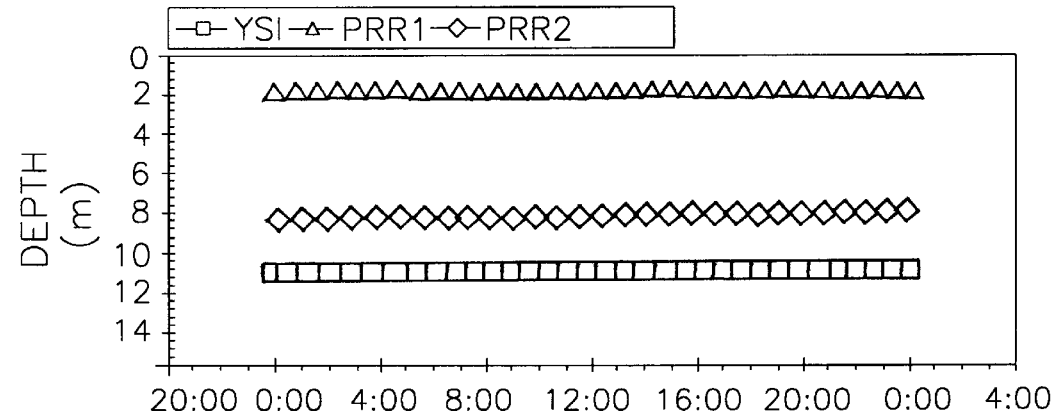
FIG. 3(f) is plot diagram showing depth curves generated by the present invention REOS-3 system.

FIGS. 3(a) through 3(f) are also part of the Daily Operation Report, showing plotted data curves. FIG. 3(a) contains plotted chlorophyll and turbidity curves. FIG. 3(b) contains plotted surface and U/W PAR curves. FIG. 3(c) contains plotted calculated transparency and kPAR curves. FIG. 3(d) contains plotted temperature curves. FIG. 3(e) contains plotted ORP curve. FIG. 3(f) contains plotted depth curves.

Figure 4A:
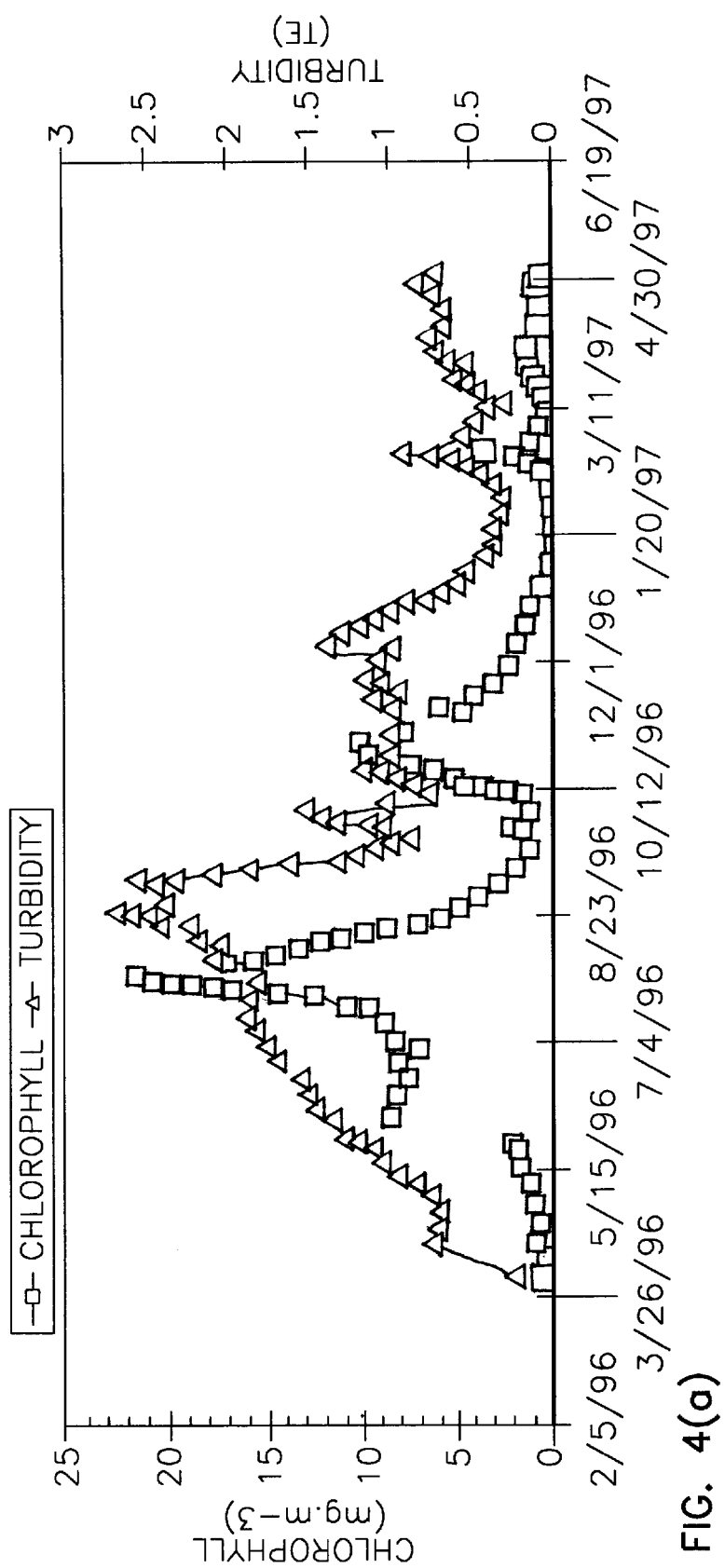
FIG. 4(a) is a plot diagram showing chlorophyll and turbidity curves over an extended time period generated by the present invention REOS-3 system.
Figure 4B:
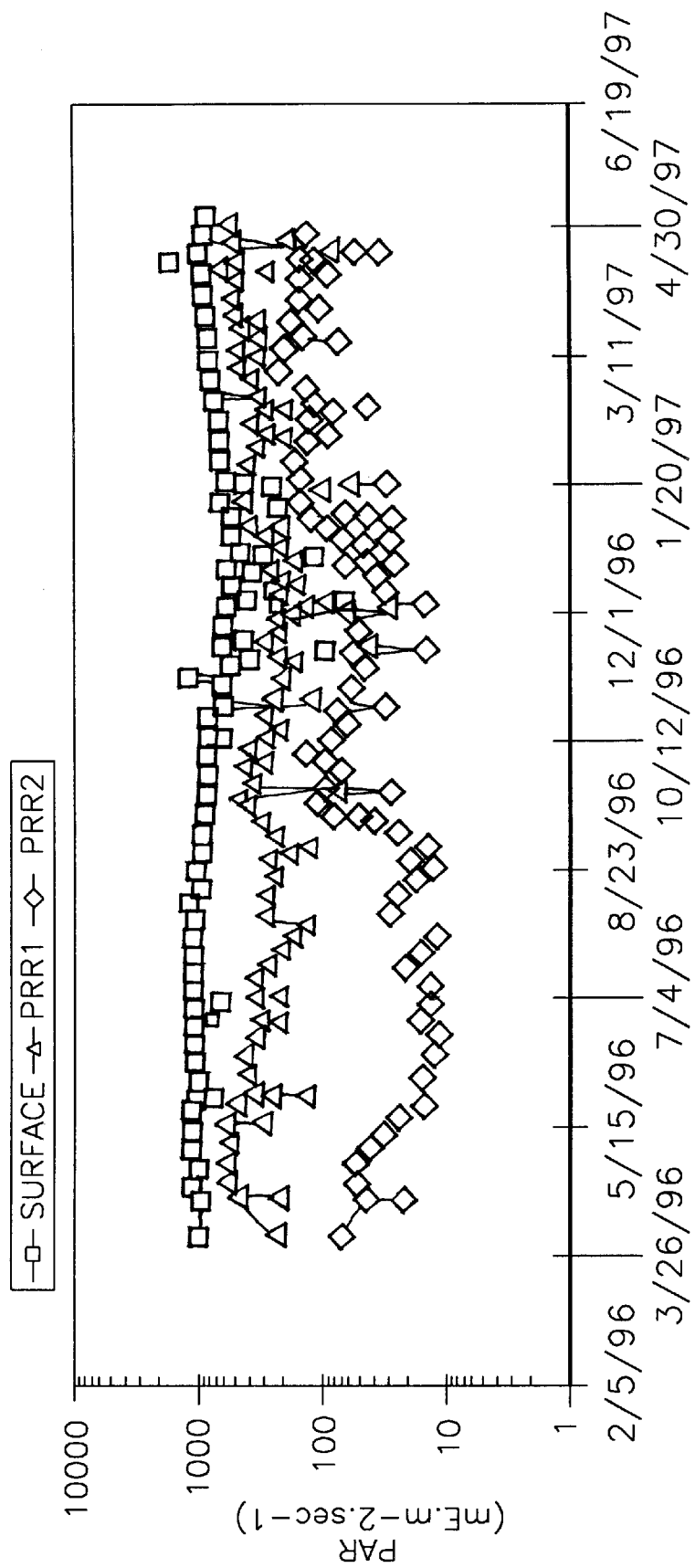
FIG. 4(b) is a plot diagram showing surface and U/W PAR curves over an extended time period generated by the present invention REOS-3 system.
Figure 4C:
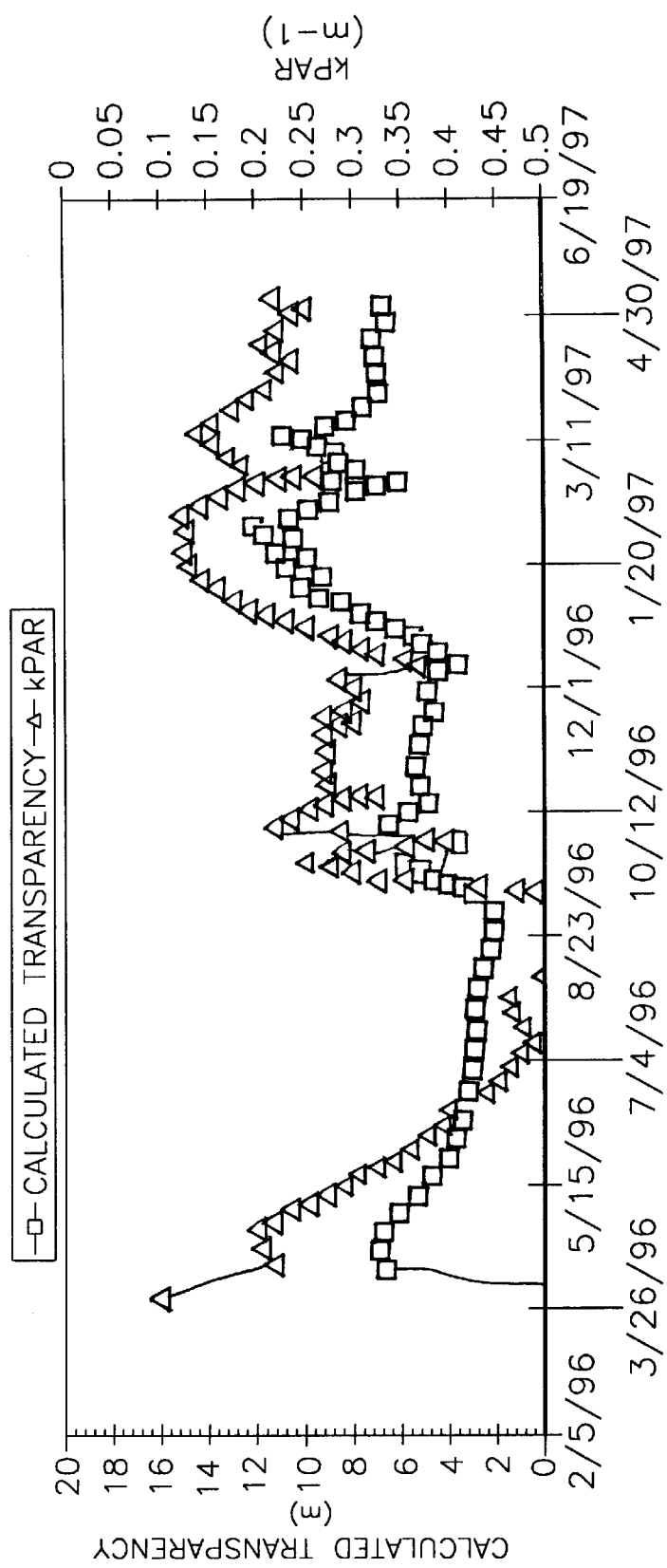
FIG. 4(c) is a plot diagram showing calculated transparency and kPAR curves over an extended time period generated by the present invention REOS-3 system.
Figure 4D:
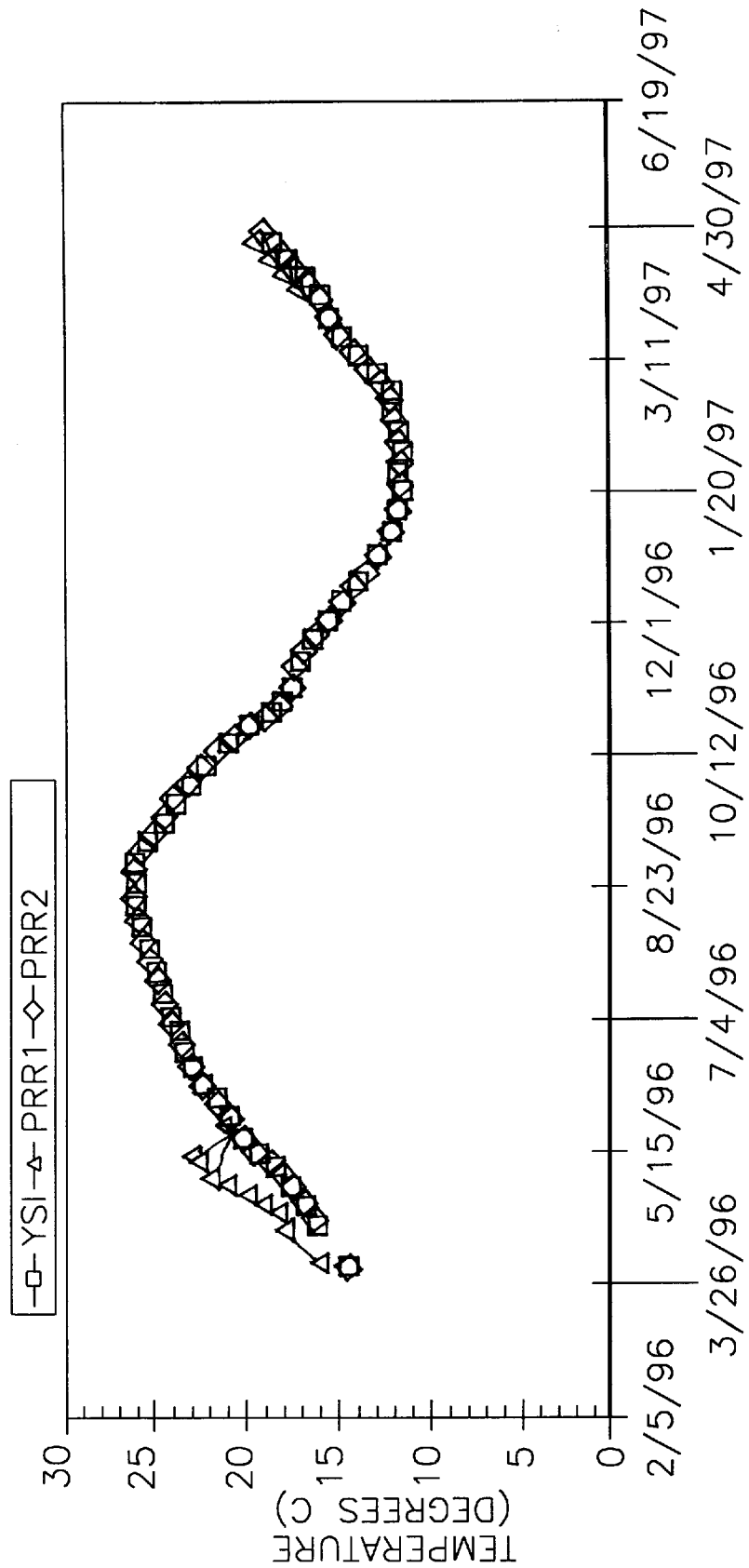
FIG. 4(d) is a plot diagram showing temperature curves over an extended time period generated by the present invention REOS-3 system.
Figure 4E:
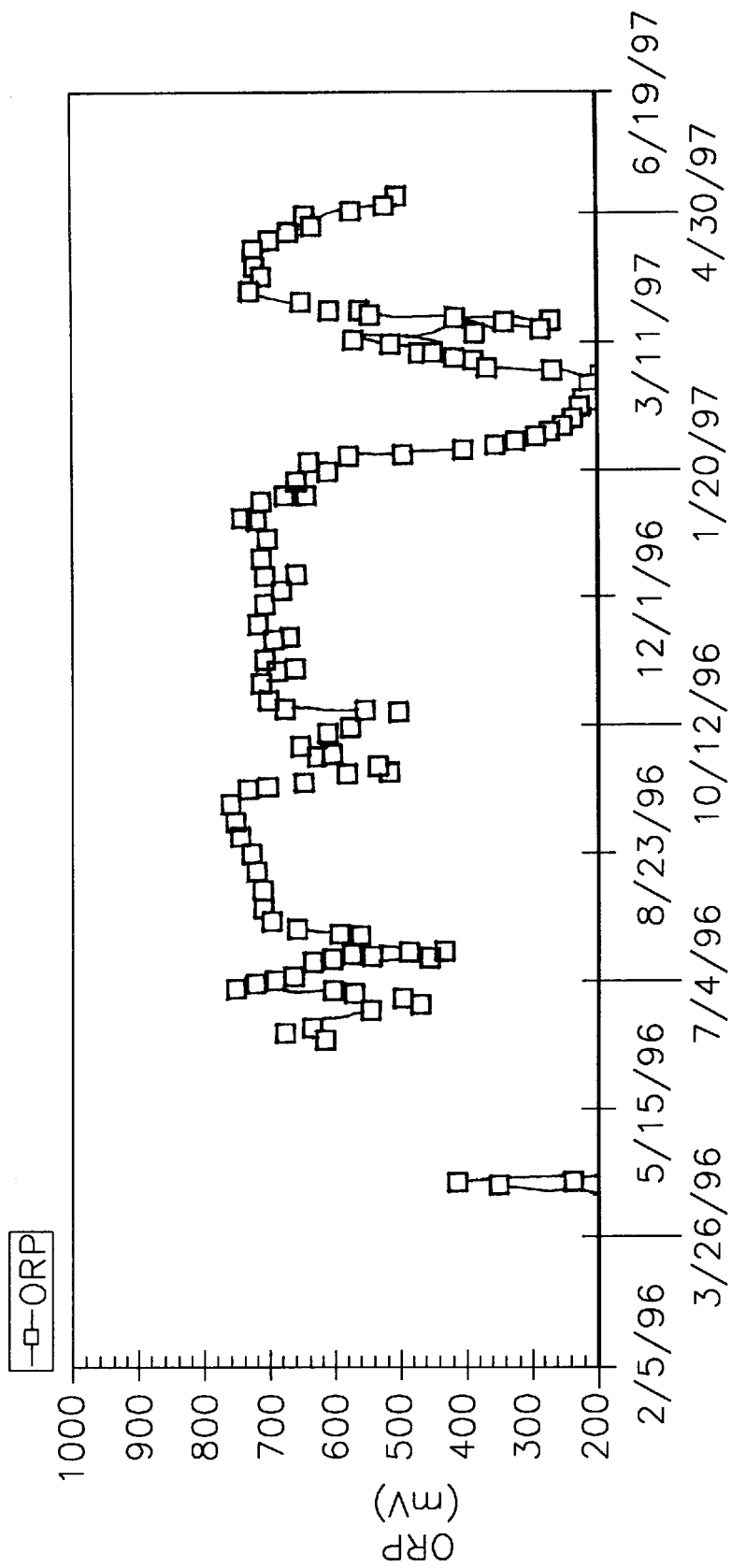
FIG. 4(e) is a plot diagram showing ORP curve over an extended time period generated by the present invention REOS-3 system.
Figure 4F:
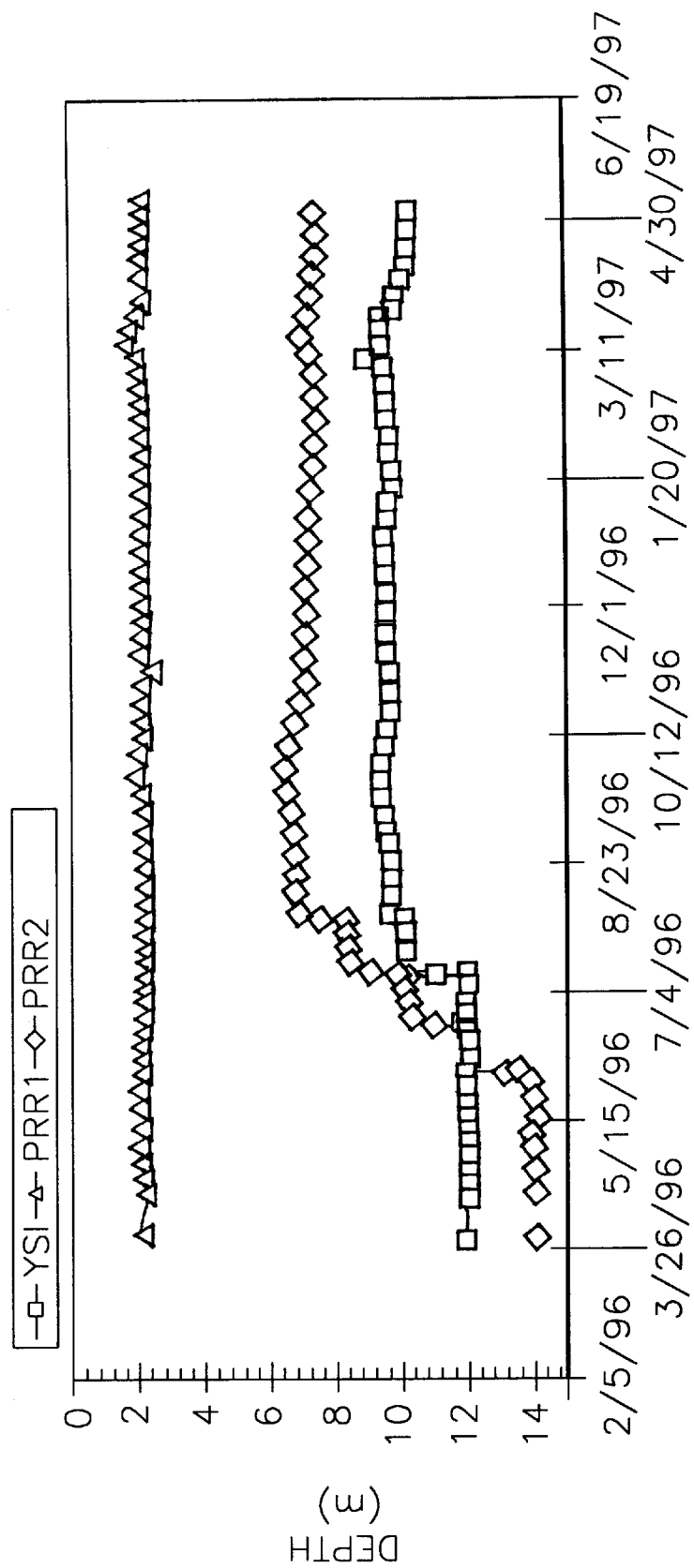
FIG. 4(f) is a plot diagram showing depth curves over an extended time period generated by the present invention REOS-3 system.

FIGS. 4(a) through 4(f) show samples of the "Extended Time Report" series generated by the present invention REOS-3 system, showing plotted data curves over an extended time period. FIG. 4(a) contains plotted chlorophyll and turbidity curves over an extended time period. FIG. 4(b) contains plotted surface and U/W PAR curves over an extended time period. FIG. 4(c) contains plotted calculated transparency and kPAR curves over an extended time period. FIG. 4(d) contains plotted temperature curves over an extended time period. FIG. 4(e) contains plotted ORP curve over an extended time period. FIG. 4(f) contains plotted depth curves over an extended time period.

Figure 5:
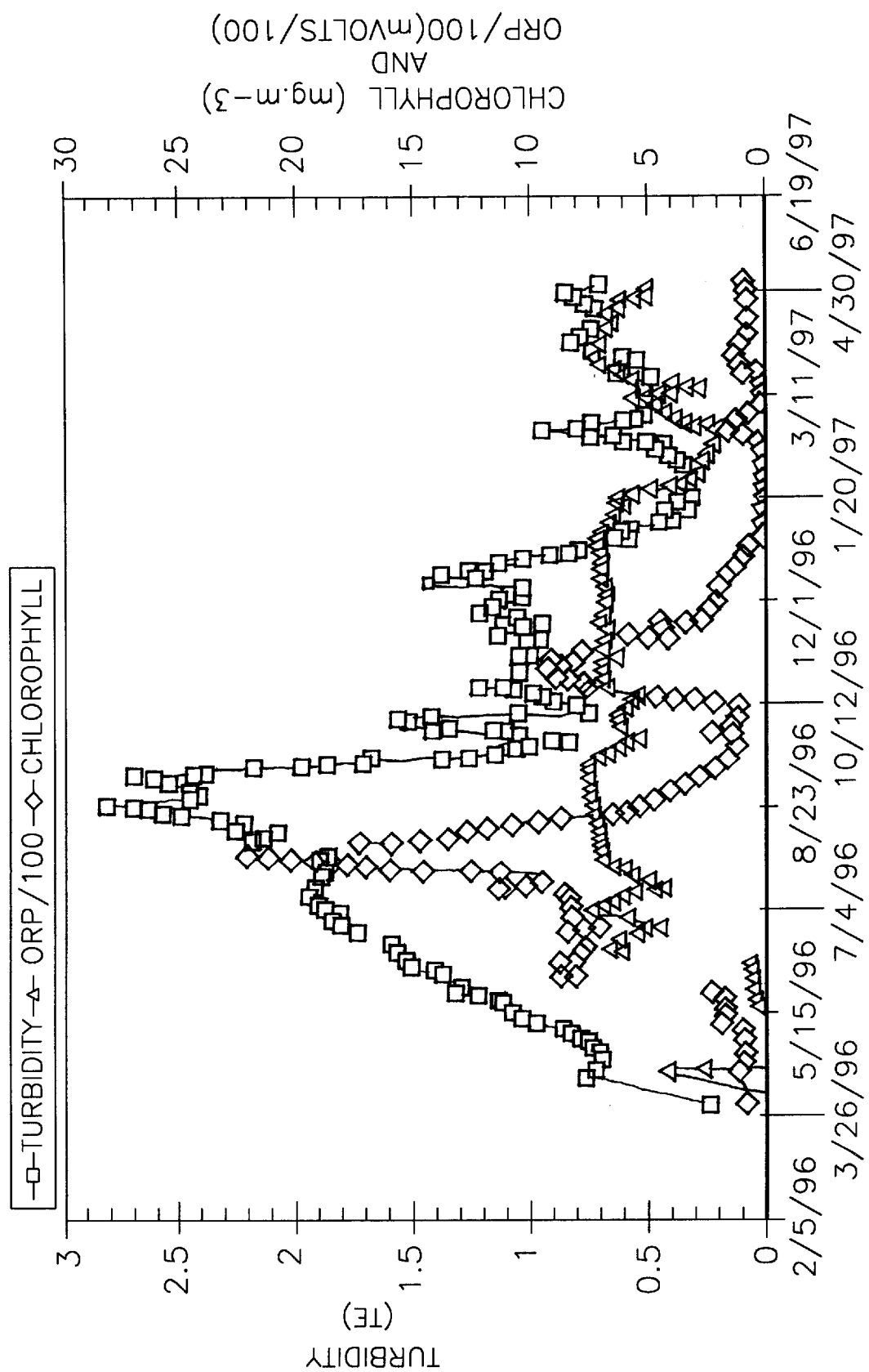
FIG. 5 is an illustrative sample of an overview report generated by the present invention REOS-3 system.

FIG. 5 shows a sample of an overview report generated by the present invention REOS-3 system, showing integrated plotted data curves over an extended time period. It contains plotted turbidity curve, ORP curve and chlorophyll curve over the extended time period, which provides a quick and easy overview of the water condition for the management of the reservoirs.

Figure 6:
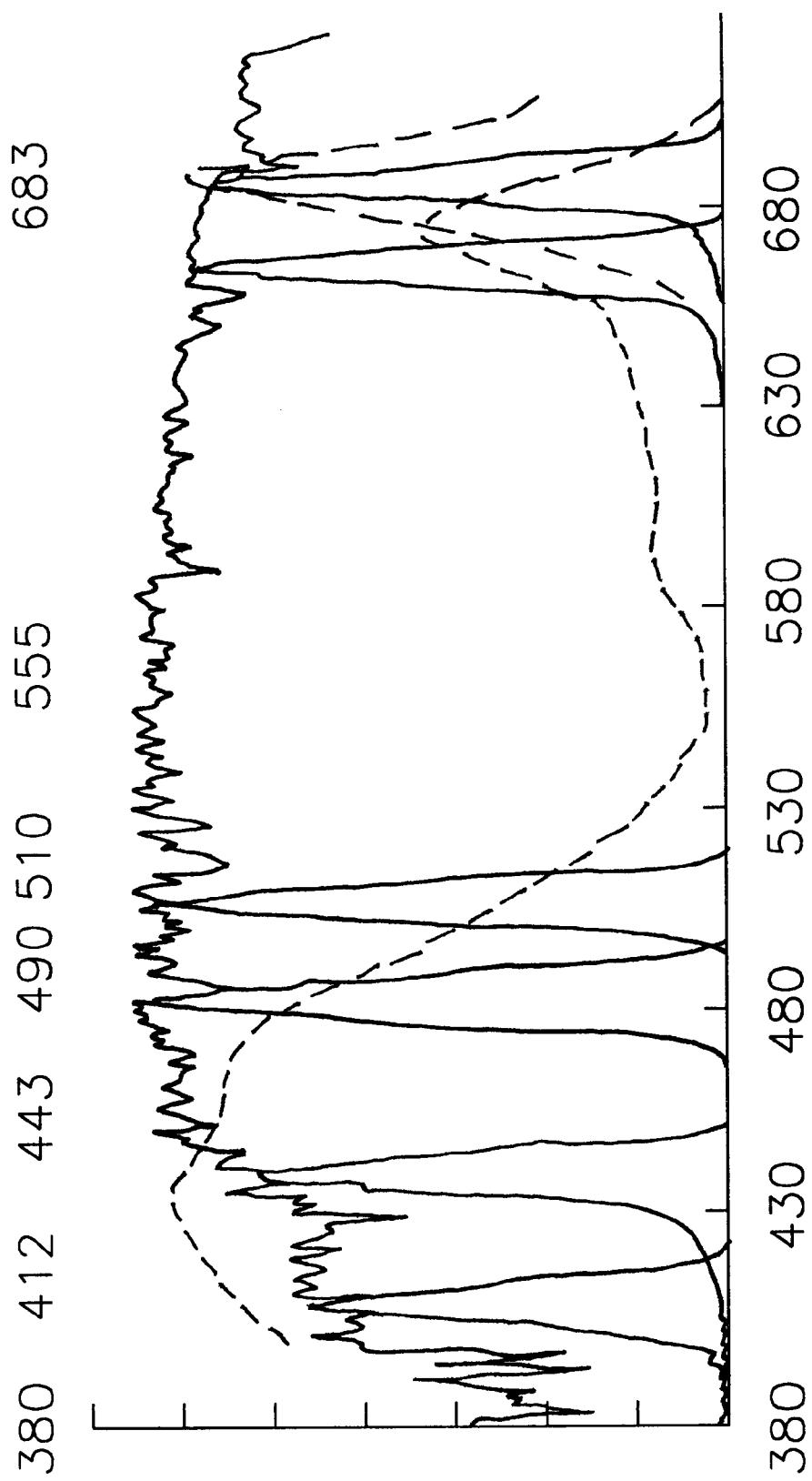
FIG. 6 is a plot diagram showing comparison of the present invention REOS-3 system 380, 412, 443, 490, 510, 555 and 683 nm multiple wavelengths channels with chlorophyll absorption and solar spectra.

The present invention also uses a new method to calculate chlorophyll concentration. Referring to FIG. 6, there is shown a typical solar spectrum contrasted with a phytoplankton absorption spectrum and the responsivity of a multichannel spectroradiometer. In the REOS-1 and REOS-2 systems, chlorophyll concentration was calculated from a measurement of natural fluorescence in the red region made by a detector centered at 683 nm. When the water column is dominated by phytoplankton, however, absorption in the blue and red regions of the spectrum cause changes in the relative spectral distribution of light in the water column. These spectral changes support other empirical approaches to the estimation of different water quality variables, such as chlorophyll concentration, transparency, turbidity and color.

Historically, specific wavelengths have been used to estimate chlorophyll concentration. Using this approach, a wide variety of algorithms have been used for making measurements of pigment. The waveband most strongly affected by phytoplankton absorption is at 443 nm relative to 555 nm, a region lightly affected by phytoplankton absorption. Changes in the ratios of reflectance or attenuation of these wavelengths are then empirically related to concentrations of pigments using statistical relationships of the type shown in Equation [1]:

$$C = aR^b \qquad [1]$$

where C is the chlorophyll concentration, R is the ratio of the reflectance or attenuation coefficient from the optical sensors and a and b are statistically derived constants. The application of ratios of either reflectance or attenuation coefficient to empirical models adds extreme flexibility to the approach, particularly as they relate to the physical position of instruments in the water column.

Reflectance $R(\lambda, z)$ is defined as the ratio of the upwelling radiance ($L_u$) to the downwelling irradiance ($E_d$) at a specific wavelength ($\lambda$) and depth (z):

$$R(\lambda, z) = L_u(\lambda, z) / E_d(\lambda, z) \qquad [2]$$

The downwelling irradiance measurement is affected by changes in the optical properties of the entire water column above the instrument; the upwelling radiance is a more local measurement since the signal arises from the region below the instrument, but is diminished by the local turbidity of the water. Reflectance is thus a measurement applied to a region "optically near" the instrument but which takes into account properties of the water column from the surface to a point below the instrument.

Attenuation coefficients $k(\lambda)$ is the rate of attenuation of the irradiance at wavelength $\lambda$ per meter of water. It is easily calculated from measurements of either $E_d$ or $L_u$ at different depths, and is completely analogous to a spectrophotometric reading over a very long pathlength:

$$k(\lambda)=ln\{E_d(\lambda,z_2)/E_d(\lambda,z_1)\}/(z_2-z_1) \quad [3]$$

where $z_2$ and $z_1$ are the respective depths of RRs 34 and 32, and $E_d(\lambda,z_2)$ is the downwelling irradiance for RR 34 and $E_d(\lambda,z_1)$ is the downwelling irradiance for RR 32 (upwelling radiance may also be used to calculate attenuation coefficient). A key advantage in the use of k in measurements of chlorophyll is that it is a sensitive integrator of the conditions of the water column between the two RRs 32 and 34.

Figure 7:
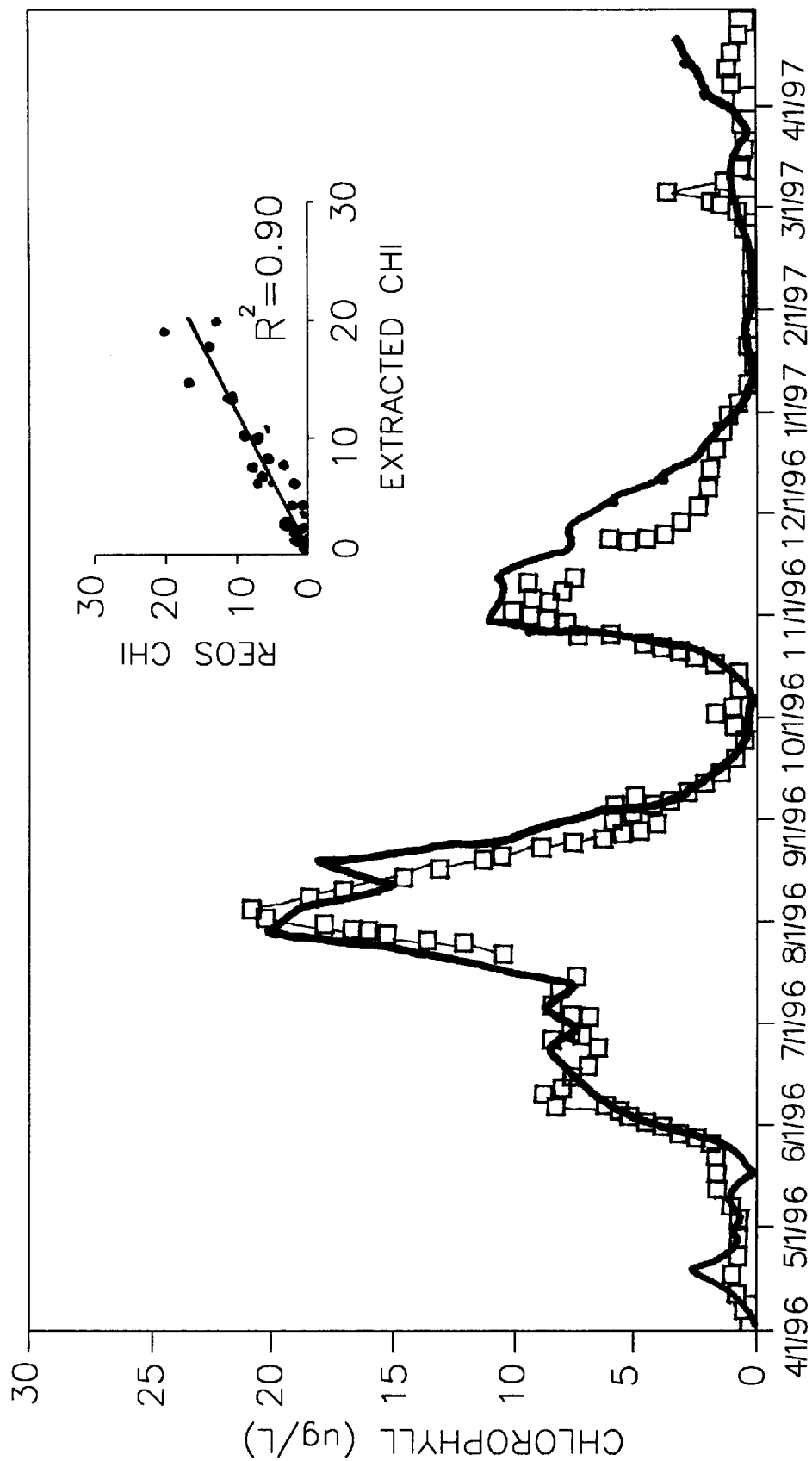
FIG. 7 is a plot diagram showing comparison of the present invention REOS-3 system chlorophyll time series with weekly surface grab sample chlorophyll extractions.

In the present invention REOS-3 system, the chlorophyll concentration is calculated by Equation [1], where R is the ratio of the downwelling attenuation coefficients at 443 nm, $k_d(443)$, and the downwelling attenuation coefficients at 555 nm, $k_d(555)$ (as computed using Equation [3]). Equation [1] was subsequently solved empirically against extracted chlorophyll values from weekly surface grab samples taken at the Lower Hollywood Reservoir outlet tower between Mar. 2, and Sep. 4, 1996. Regression analysis for this time period yields values for a of 0.0529 and b of 4.6803. FIG. 7 illustrates the relationship between the extracted surface chlorophyll values and the calculated REOS-3 water column values.

Weekly turbidity measurements made in the field with a Hach 2100P turbidimeter of surface grab samples taken at the Hollywood Reservoir outlet tower between March 2, and Sep. 4, 1996 were compared to REOS-3 spectral attenuation measurements over the same period. All wavelength channels of the RRs were statistically compared with the turbidity measurement using linear, logarithmic, exponential, and polynomial transformations of the data. The goal was to develop an empirical relationship between nephelometric turbidity unit (NTU) turbidity and water transparency over the visible spectrum. Ultimately, the most robust relationship was found to be a linear equation relating the measured turbidity in NTU's to the attenuation coefficient over the entire visible spectrum, where the unit of this relationship is termed "Turbidity Equivalents" (TE):

$$TE=4.8354 \cdot k(PAR)-0.3435 \quad [4]$$

Figure 8:
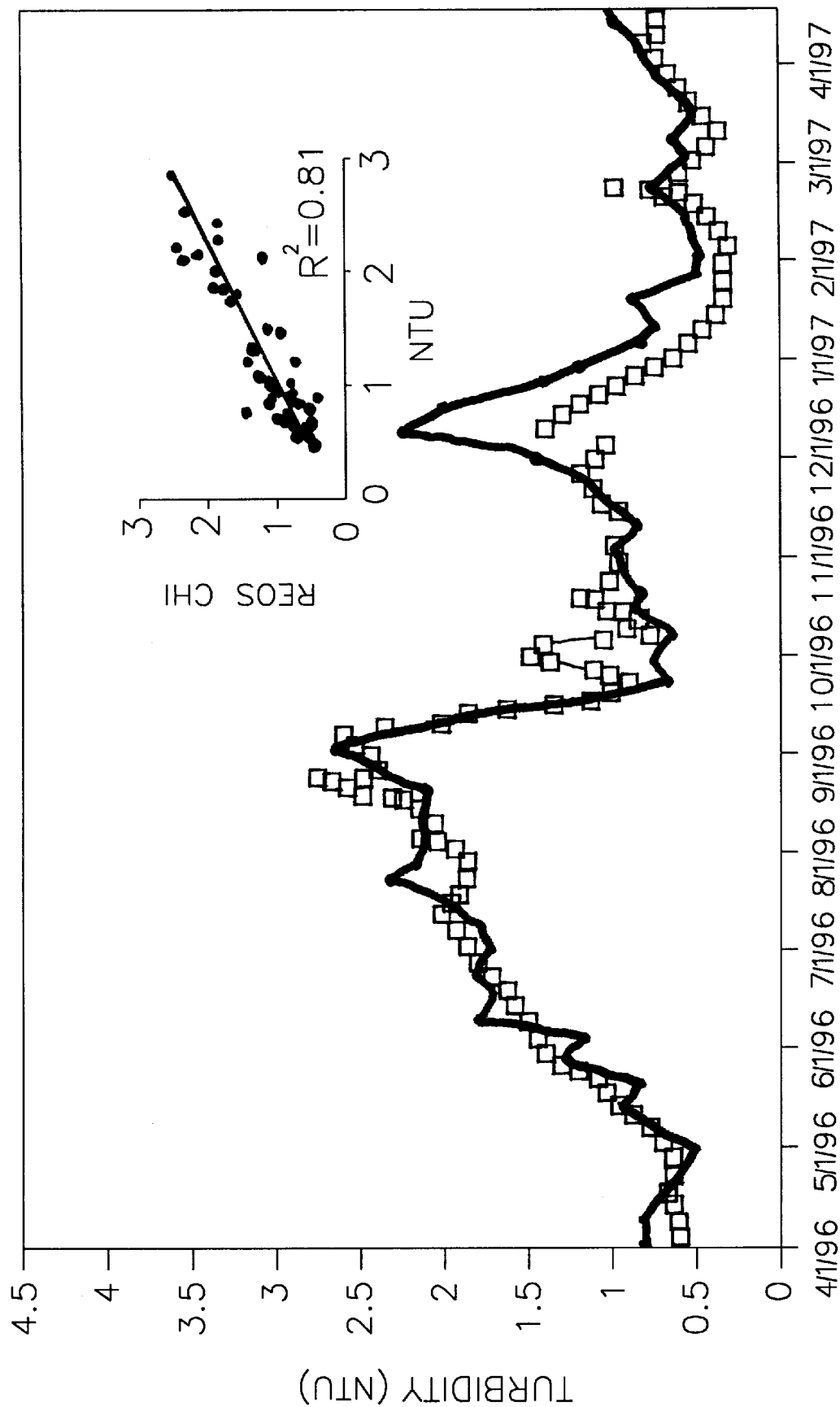
FIG. 8 is a plot diagram showing comparison of the present invention REOS-3 system water column turbidity equivalent (TE) time series with weekly surface grab sample nephelometric turbidity unit (NTU) field measurements.

FIG. 8 illustrates the relationship between the nephelometric measurements and the calculated REOS-3 water column TE Values.

The present invention RR-based REOS-3 system has all the benefits of the PNF-based REOS-1 and REOS-2 systems, but offers several advantages over what was available. Unlike the REOS-1 and REOS-2 PNF-based technology, which uses one 400–700 nm broadband sensor for visible light, the REOS-3 RR-based approach breaks up the downwelling spectrum into 7 narrowband channels in strategic wavebands. Relative changes in these spectral regions can be used to predict concentrations of chlorophyll higher than the usable range of the Natural Fluorescence sensor. It is also noted that the changes in the wavebands may be related to changes in other constituents of the water, such as detritus, cyanobacteria, and colored dissolved substances. The utility of these wavebands for monitoring substances other than chlorophyll, such as bacterial concentration, requires validation and is the subject of additional research. However, the in situ database that will be developed from this approach may be invaluable.

Furthermore, the present invention REOS-3 system monitors the decrease in light for the bio-optically active region of the water column from the surface down to each RR instrument and not just a section under each instrument. Changes in the optical properties are integrated over the water column and are provided in addition to the natural fluorescence data. This modification tackles the problems associated with particle stratification.

PNF-based measurements of chlorophyll and primary production have been validated throughout the world, and have been found to work well in a wide range of conditions. However, the accuracy of the measurements of chlorophyll decreases as concentrations increase above 7 mg/m$^3$, such as in the middle of a bloom. This decrease in accuracy occurs because at high concentrations, chlorophyll itself begins to absorb the red fluorescence and the signal never reaches the detector on the instrument. In addition, high concentrations of dissolved materials or small particles that absorb strongly in the red part of the spectrum may mask the fluorescence from the crop. These conditions will also reduce the fluorescent flux from the phytoplankton crop and will not be efficiently picked up by the PNF. Under these extreme conditions, chlorophyll concentration and photosynthetic rates as predicted by the PNF-based systems will underestimate the actual values. Furthermore, stratification in deeper reservoirs may require increased numbers of instruments to preclude the chance of missing blooms in stratified conditions.

In addition to natural fluorescence and PAR measurements, the use of the RR multiple wavelengths spectroradiometer affords collecting additional information about the reservoir system. The strength of the multiple wavelengths approach is that more than one optical algorithm can be applied to the measurement, resulting in increased analytical flexibility. Secondly, a wider range of conclusions can be drawn about the state of the water column because regions of the entire solar spectrum can be monitored individually.

Defined in detail, the present invention is an improved water quality monitoring system, comprising: (a) a mooring assembly; (b) an array of underwater measurement devices suspended underwater by the mooring assembly, and including at least one reflectance radiometer for measuring multiple wavelengths of upwelling radiance and utilizing a cosine collector for measuring multiple wavelengths of downwelling irradiance, which can be used to calculate chlorophyll concentration in the water; (c) a remote access workstation for processing and storing data measured by the array of underwater measurement devices; and (d) a remote data spooler device for communicating the data measured by the array of underwater measurement devices to the remote access workstation.

Defined broadly, the present invention is an improved water quality monitoring system, comprising: (a) an array of underwater measurement devices moored underwater and including at least one reflectance radiometer for measuring multiple wavelengths of downwelling irradiance and upwelling radiance which can be used to calculate chlorophyll concentration in the water; and (b) a remote access workstation communicating with the array of underwater measurement devices for processing and storing data measured by the array of underwater measurement devices.

Defined more broadly, the present invention is an improved water quality monitoring system, comprising at least one underwater measurement device for measuring multiple wavelengths of downwelling irradiance or upwelling radiance for calculation of chlorophyll concentration in the water.

Alternatively defined in detail, the present invention is an improved method of monitoring water quality, comprising the steps of: (a) providing a mooring assembly; (b) suspending an array of underwater measurement devices underwater by the mooring assembly, providing at least one reflectance radiometer measuring multiple wavelengths of upwelling radiance and utilizing a cosine collector to measure multiple wavelengths of downwelling irradiance; (c) communicating data measured by the array of underwater measurement devices to a remote access workstation; (d) processing and storing data measured by the array of underwater measurement devices; and (e) calculating attenuation coefficients from the downwelling irradiance or upwelling radiance to derive chlorophyll concentration in the water.

Alternatively defined broadly, the present invention is an improved method of monitoring water quality, comprising the steps of: (a) mooring an array of measurement devices underwater, including at least one reflectance radiometer to measure multiple wavelengths of downwelling irradiance and upwelling radiance; (b) communicating data measured by the array of underwater measurement devices to a remote access workstation for data processing and storage; (c) calculating attenuation coefficients from the downwelling irradiance or upwelling radiance to derive chlorophyll concentration in the water.

Alternatively defined more broadly, the present invention is an improved method of monitoring water quality, comprising the steps of utilizing at least one underwater measurement device to measure multiple wavelengths of downwelling irradiance or upwelling radiance, and calculating attenuation coefficients from the downwelling irradiance or upwelling radiance to derive chlorophyll concentration in the water.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. An improved water quality monitoring system, comprising:
   a. a mooring assembly;
   b. an array of underwater measurement devices suspended underwater by said mooring assembly, and including at least one reflectance radiometer for measuring multiple wavelengths of upwelling radiance and utilizing a cosine collector for measuring multiple wavelengths of downwelling irradiance, which can be used to calculate chlorophyll concentration in the water;
   c. a remote access workstation for processing and storing data measured by said array of underwater measurement devices; and
   d. a remote data spooler device for communicating said data measured by said array of underwater measurement devices to said remote access workstation.

2. The improved water quality monitoring system as defined in claim 1, wherein said array of underwater measurement devices comprises a first reflectance radiometer located near the water surface, and a second reflectance radiometer located below and spaced apart from the first reflectance radiometer.

3. The improved water quality monitoring system as defined in claim 1, wherein said at least one reflectance radiometer has a plurality of top channels for measuring downwelling irradiance.

4. The improved water quality monitoring system as defined in claim 1, wherein said at least one reflectance radiometer has a plurality of bottom channels for measuring upwelling radiance.

5. The improved water quality monitoring system as defined in claim 1, wherein said cosine collector has a flat collector surface responsive to $2\pi$ steradians solid angle.

6. The improved water quality monitoring system as defined in claim 5, wherein said cosine collector has an outer rim leveled with said flat collector surface and acting as an occluding ring.

7. The improved water quality monitoring system as defined in claim 1, wherein said remote data spooler device communicates with said remote access workstation through wired communication means.

8. The improved water quality monitoring system as defined in claim 1, wherein said remote data spooler device communicates with said remote access workstation through wireless communication means.

9. An improved water quality monitoring system, comprising:
   a. an array of underwater measurement devices moored underwater and including at least one reflectance radiometer for measuring multiple wavelengths of downwelling irradiance and upwelling radiance which can be used to calculate chlorophyll concentration in the water; and
   b. a remote access workstation communicating with said array of underwater measurement devices for processing and storing data measured by said array of underwater measurement devices.

10. The improved water quality monitoring system as defined in claim 9, wherein said array of underwater measurement devices comprises a first reflectance radiometer located near the water surface, and a second reflectance radiometer located below and spaced apart from the first reflectance radiometer.

11. The improved water quality monitoring system as defined in claim 9, wherein said at least one reflectance radiometer has a plurality of top channels for measuring downwelling irradiance.

12. The improved water quality monitoring system as defined in claim 9, wherein said at least one reflectance radiometer has a plurality of bottom channels for measuring upwelling radiance.

13. The improved water quality monitoring system as defined in claim 9, wherein said at least one reflectance radiometer utilizes a cosine collector with a flat collector surface responsive to $2\pi$ steradians solid angle.

14. The improved water quality monitoring system as defined in claim 9, wherein said remote access work station communicates with said array of underwater measurement devices through wired communication means.

15. The improved water quality monitoring system as defined in claim 9, wherein said remote access work station communicates with said array of underwater measurement devices through wireless communication means.

16. An improved water quality monitoring system, comprising at least one underwater measurement device for measuring multiple wavelengths of downwelling irradiance or upwelling radiance for calculation of chlorophyll concentration in the water.

17. The improved water quality monitoring system as defined in claim 16, wherein said at least one underwater measurement device has a plurality of top channels for measuring downwelling irradiance.

18. The improved water quality monitoring system as defined in claim 16, wherein said at least one underwater measurement device has a plurality of bottom channels for measuring upwelling radiance.

19. The improved water quality monitoring system as defined in claim 16, wherein said at least one underwater measurement device utilizes a cosine collector with a flat collector surface responsive to $2\pi$ steradians solid angle.

20. An improved method of monitoring water quality, comprising the steps of:
   a. providing a mooring assembly;
   b. suspending an array of underwater measurement devices underwater by said mooring assembly, providing at least one reflectance radiometer measuring multiple wavelengths of upwelling radiance and utilizing a cosine collector to measure multiple wavelengths of downwelling irradiance;
   c. communicating data measured by said array of underwater measurement devices to a remote access workstation;
   d. processing and storing data measured by said array of underwater measurement devices; and
   e. calculating attenuation coefficients from said downwelling irradiance or upwelling radiance to derive chlorophyll concentration in the water.

21. An improved method of monitoring water quality, comprising the steps of:
   a. mooring an array of measurement devices underwater, including at least one reflectance radiometer to measure multiple wavelengths of downwelling irradiance and upwelling radiance;
   b. communicating data measured by said array of underwater measurement devices to a remote access workstation for data processing and storage;
   c. calculating attenuation coefficients from said downwelling irradiance or upwelling radiance to derive chlorophyll concentration in the water.

\* \* \* \* \*

UNITED STATES PATENT AND TRADEMARK OFFICE
CERTIFICATE OF CORRECTION

PATENT NO. : 5,905,570
DATED : May 18, 1999
INVENTOR(S) : Brian N. White and John H. Morrow It is certified that error appears in the above-identified patent and that said Letters Patent is hereby corrected as shown below:

ON THE TITLE PAGE:
Item [73] Assignee should read --

Department of Water and Power City of Los Angeles,
Los Angeles;

Biospherical Instruments Inc.,
San Diego, both of California; part interest
to each --.

Signed and Sealed this

Twenty-second Day of February, 2000

Attest:

Q. TODD DICKINSON

*Attesting Officer*    *Commissioner of Patents and Trademarks*